United States Patent
Binder et al.

(10) Patent No.: US 8,048,649 B2
(45) Date of Patent: Nov. 1, 2011

(54) **PRODUCTION OF AMINO ACIDS FROM SUCROSE IN *CORYNEBACTERIUM GLUTAMICUM***

(75) Inventors: Thomas P. Binder, Decatur, IL (US); Paul D. Hanke, Urbana, IL (US)

(73) Assignee: Archer Daniels Midland Company, Decatur, IL (US)

( * ) Notice: Subject to any disclaimer, the term of this patent is extended or adjusted under 35 U.S.C. 154(b) by 0 days.

(21) Appl. No.: 12/239,242

(22) Filed: Sep. 26, 2008

(65) Prior Publication Data

US 2009/0081740 A1 Mar. 26, 2009

Related U.S. Application Data

(60) Provisional application No. 60/995,348, filed on Sep. 26, 2007.

(51) Int. Cl.
*C12P 13/08* (2006.01)
*C12N 9/12* (2006.01)
*C12N 9/22* (2006.01)
*C12N 1/21* (2006.01)

(52) U.S. Cl. ...... 435/115; 435/194; 435/234; 435/252.3

(58) Field of Classification Search .................. 435/115, 435/194, 234, 252.3
See application file for complete search history.

(56) References Cited

U.S. PATENT DOCUMENTS

| | | | |
|---|---|---|---|
| 6,884,614 B1 * | 4/2005 | Pompejus et al. ......... | 435/252.3 |
| 2002/0127650 A1 | 9/2002 | Curtis | |
| 2003/0082595 A1 | 5/2003 | Jiang et al. | |
| 2005/0181488 A1 | 8/2005 | Akhverdian et al. | |
| 2006/0281908 A1 | 12/2006 | Callen | |
| 2007/0134768 A1 | 6/2007 | Zelder et al. | |

OTHER PUBLICATIONS

U.S. Sugar Corp., Molasses Composition, United States Sugar Corporation, Molasses & Liquid Feeds Div., http://www.suga-lik.com/molasses/composition. html, 2003.*

International Preliminary Report on Patentability for PCT/US08/77879 dated Jun. 2, 2010 (Form PCT/IPEA/416 & PCT/IPEA/409).

Tanaka et al., Regulation of the Expression of Phosphoenolpyruvate: Carbohydrate Phosphotransferase System (PTS) Genes in *Corynebacterium glutamicum* R, Microbiology (2008) 154, 264-274.

(Continued)

*Primary Examiner* — Rosanne Kosson
(74) *Attorney, Agent, or Firm* — Mark W. Roberts

(57) ABSTRACT

Methods and compositions for increased production of amino acids from *C. glutamicum* using sucrose as a carbon source are described. In one aspect, increased production of L-lysine from *C. glutamicum* is accomplished by using a strain having a mutation in the ptsF gene encoding fructose-PTS enzyme that attenuates or blocks fructose import into the cell when such strain is grown on media containing sucrose as a carbon source and production is increased by providing glucose isomerase in the fermentation media. The glucose isomerase may be exogenously added or expressed in the strain and exported into the media. In certain embodiments the media also contain an invertase. In another aspect increased production of L-lysine is accomplished by making a *C. glutamicum* strain having the ptsF mutation and a second mutation in a fructose exporter function. The dual mutation retains imported fructose in the cell. In certain embodiments, the strain also overexpresses at least one of a glucose isomerase and glucokinase activity in the cell to drive imported fructose toward the pentose phosphate pathway to increase L-lysine production.

8 Claims, 6 Drawing Sheets

OTHER PUBLICATIONS

Deutscher et al., How Phosphotransferase System-Related Protein Phosphorylation Regulates Carbohydrate Metabolism in Bacteria, Microbiology and Molecular Biology Reviews, Dec. 2006, vol. 70, No. 4, pp. 939-1031.

Moon et al., Analyses of Enzyme II Gene Mutants for Sugar Transport and Heterologous Expression of Fructokinase Gene in *Corynebacterium glutamicum* ATCC 13032, FEMS Microbiology Letters 244 (2005) 259-266.

Dominguez et al., New and Simple Plate Test for Screening Relative Transfructosylation Activity of Fungi, Rev. Iberoam Micol 2006; 23: 189-191.

Wittmann et al., Metabolic Fluxes in *Corynebacterium glutamicum* during Lysine Production with Sucrose as Carbon Source, Applied and Environmental Microbiology, Dec. 2004, p. 7277-7287.

Kiefer et al., Influence of Glucose, Fructose and Sucrose as Carbon Sources on Kinetics and Stoichiometry of Lysine Production by *Corynebacterium glutamicum*, Journal of Industrial Microbiology & Biotechnology (2002) 28, 338-343.

Follstad et al., Effect of Reversible Reactions on Isotope Label Redistribution, Analysis of the Pentose Phosphate Pathway, Eur. J. Biochem. (1998) 252, 360-371.

Dominguez et al., Carbon-Flux Distribution in the Central Metabolic Pathways of *Corynebacterium glutamicum* during Growth on Fructose, Eur. J. Biochem. (1998) 254, 96-102.

Hahn-Hagerdal et al., Improved Ethanol Production from Xylose with Glucose Isomerase and *Saccharomyces cerevisiae* using the Respiratory Inhibitor Azide, Appl. Microbiol Biotechnol (1986) 24: 287-293.

Georgi et al., Lysine and Glutamate Production by *Corynebacterium glutamicum* on Glucose, Fructose and Sucrose: Roles of Malic Enzyme and Fructose-1,6-Biophosphatase, Metabolic Engineering (2005) vol. 7, 291-301.

Dominguez et al., Complete Sucrose Metabolism Requires Fructose Phosphotransferase Activity in *Corynebacterium glutamicum* to Ensure Phosphorylation of Liberated Fructose, Applied and Environmental Microbiology, Oct. 1996, vol. 62, No. 10, p. 3878-3880.

Kiefer et al., Comparative Metabolic Flux Analysis of Lysine-Producing *Corynebacterium glutamicum* Cultured on Glucose or Fructose, Applied and Environmental Microbiology, Jan. 2004, vol. 70, No. 1, p. 229-239.

Shah et al., Fermentative Production of L-Lysine Bacterial Fermentation-I, May-Jun. 2002, J. Med. Sci. 2 (3): 152-157.

Wittmann et al., Metabolic Fluxes in *Corynebacterium glutamicum* during Lysine Production with Sucrose as a Carbon Source, Applied and Environmental Microbiology, Dec. 2004, vol. 70, No. 12, p. 7277-7287.

Wittmann et al., Application of MALDI-TOF MS to Lysine-Producing *Corynebacterium glutamicum*, a Novel Approach for Metabolic Flux Analysis, Eur. J. Biochem. 268 (2001), p. 2441-2455.

International Search Report dated Dec. 11, 2008.

Moon et al., "Analyses of Enzyme II Gene Mutants for Sugar Transport and Heterologous Expression of Fructokinase Gene in *Corynebacterium glutamicum* ATCC 13032", FEMS Micobiol. Lett. 2005, vol. 244, pp. 259-266, Abstract.

Deutscher et al, How Phosphotransferase System-Related Protein Phosphorylation Regulates Carbohydrate Metabolism in Bacteria, Microbiology and Molecular Biology Reviews, Dec. 2006, pp. 939-1031,vol. 70, No. 4, American Society for Microbiology, USA.

Deutscher et al, Author's Correction How Phosphotransferase System-Related Protein Phosphorylation Regulates Carbohydrate Metabolism in Bacteria, Microbiology and Molecular Biology Reviews, Sep. 2008, p. 555,vol. 72, No. 3, Microbiology and Molecular Biology Reviews, USA.

Tanaka et al, Regulation of the expression of Phosphoenolpyruvate: carbohydrate phosphotransferase system (PTS) genes in *Corynebacterium glutamicum* R, Microbiology 154, 2008, pp. 264-274, Research Institute of Innovative Technology for the Earth, Japan.

* cited by examiner

Fig. 1 (wild type)

SEQUENCE LISTING

```
<160> NUMBER OF SEQ ID NOS: 12

<210> SEQ ID NO 1
<211> LENGTH: 688
<212> TYPE: PRT
<213> ORGANISM: Corynebacterium glutamicum

<400> SEQUENCE: 1

Met Asn Ser Val Asn Asn Ser Ser Leu Val Arg Leu Asp Val Asp Phe
1               5                   10                  15

Gly Asp Ser Thr Thr Asp Val Ile Asn Asn Leu Ala Thr Val Ile Phe
            20                  25                  30

Asp Ala Gly Arg Ala Ser Ser Ala Asp Ala Leu Ala Lys Asp Ala Leu
        35                  40                  45

Asp Arg Glu Ala Lys Ser Gly Thr Gly Val Pro Gly Gln Val Ala Ile
    50                  55                  60

Pro His Cys Arg Ser Glu Ala Val Ser Val Pro Thr Leu Gly Phe Ala
65                  70                  75                  80
```

-continued

Arg Leu Ser Lys Gly Val Asp Phe Ser Gly Pro Asp Gly Asp Ala Asn
            85                  90                  95
Leu Val Phe Leu Ile Ala Ala Pro Ala Gly Gly Lys Glu His Leu
        100                 105                 110
Lys Ile Leu Ser Lys Leu Ala Arg Ser Leu Val Lys Lys Asp Phe Ile
            115                 120                 125
Lys Ala Leu Gln Glu Ala Thr Thr Glu Gln Glu Ile Val Asp Val Val
        130                 135                 140
Asp Ala Val Leu Asn Pro Ala Pro Lys Thr Thr Glu Pro Ala Ala Ala
145                 150                 155                 160
Pro Ala Ala Ala Val Ala Glu Ser Gly Ala Ala Ser Thr Ser Val
                165                 170                 175
Thr Arg Ile Val Ala Ile Thr Ala Cys Pro Thr Gly Ile Ala His Thr
            180                 185                 190
Tyr Met Ala Ala Asp Ser Leu Thr Gln Asn Ala Glu Gly Arg Asp Asp
        195                 200                 205
Val Glu Leu Val Val Glu Thr Gln Gly Ser Ser Ala Val Thr Pro Val
        210                 215                 220
Asp Pro Lys Ile Ile Glu Ala Ala Asp Ala Val Ile Phe Ala Thr Asp
225                 230                 235                 240
Val Gly Val Lys Asp Arg Glu Arg Phe Ala Gly Lys Pro Val Ile Glu
            245                 250                 255
Ser Gly Val Lys Arg Ala Ile Asn Glu Pro Ala Lys Met Ile Asp Glu
            260                 265                 270
Ala Ile Ala Ala Ser Lys Asn Pro Asn Ala Arg Lys Val Ser Gly Ser
        275                 280                 285
Gly Val Ala Ala Ser Ala Glu Thr Thr Gly Glu Lys Leu Gly Trp Gly
        290                 295                 300
Lys Arg Ile Gln Gln Ala Val Met Thr Gly Val Ser Tyr Met Val Pro
305                 310                 315                 320
Phe Val Ala Ala Gly Gly Leu Leu Leu Ala Leu Gly Phe Ala Phe Gly
            325                 330                 335
Gly Tyr Asp Met Ala Asn Gly Trp Gln Ala Ile Ala Thr Gln Phe Ser
            340                 345                 350
Leu Thr Asn Leu Pro Gly Asn Thr Val Asp Val Asp Gly Val Ala Met
        355                 360                 365
Thr Phe Glu Arg Ser Gly Phe Leu Leu Tyr Phe Gly Ala Val Leu Phe
        370                 375                 380
Ala Thr Gly Gln Ala Ala Met Gly Phe Ile Ala Ala Leu Ser Gly
385                 390                 395                 400
Tyr Thr Ala Tyr Ala Leu Ala Gly Arg Pro Gly Ile Ala Pro Gly Phe
            405                 410                 415
Val Gly Gly Ala Ile Ser Val Thr Ile Gly Ala Gly Phe Ile Gly Gly
            420                 425                 430
Leu Val Thr Gly Ile Leu Ala Gly Leu Ile Ala Leu Trp Ile Gly Ser
        435                 440                 445
Trp Lys Val Pro Arg Val Val Gln Ser Leu Met Pro Val Ile Ile
        450                 455                 460
Pro Leu Leu Thr Ser Val Val Gly Leu Val Met Tyr Leu Leu Leu
465                 470                 475                 480
Gly Arg Pro Leu Ala Ser Ile Met Thr Gly Leu Gln Asp Trp Leu Ser
            485                 490                 495
Ser Met Ser Gly Ser Ser Ala Ile Leu Leu Gly Ile Ile Leu Gly Leu
            500                 505                 510

```
Met Met Cys Phe Asp Leu Gly Gly Pro Val Asn Lys Ala Ala Tyr Leu
        515                 520                 525

Phe Gly Thr Ala Gly Leu Ser Thr Gly Asp Gln Ala Ser Met Glu Ile
    530                 535                 540

Met Ala Ala Ile Met Ala Ala Gly Met Val Pro Pro Ile Ala Leu Ser
545                 550                 555                 560

Ile Ala Thr Leu Leu Arg Lys Lys Leu Phe Thr Pro Ala Glu Gln Glu
            565                 570                 575

Asn Gly Lys Ser Ser Trp Leu Leu Gly Leu Ala Phe Val Ser Glu Gly
                580                 585                 590

Ala Ile Pro Phe Ala Ala Ala Asp Pro Phe Arg Val Ile Pro Ala Met
        595                 600                 605

Met Ala Gly Gly Ala Thr Thr Gly Ala Ile Ser Met Ala Leu Gly Val
    610                 615                 620

Gly Ser Arg Ala Pro His Gly Gly Ile Phe Val Val Trp Ala Ile Glu
625                 630                 635                 640

Pro Trp Trp Gly Trp Leu Ile Ala Leu Ala Ala Gly Thr Ile Val Ser
            645                 650                 655

Thr Ile Val Val Ile Ala Leu Lys Gln Phe Trp Pro Asn Lys Ala Val
                660                 665                 670

Ala Ala Glu Val Ala Lys Gln Glu Ala Gln Gln Ala Ala Val Asn Ala
        675                 680                 685

<210> SEQ ID NO 2
<211> LENGTH: 2067
<212> TYPE: DNA
<213> ORGANISM: Corynebacterium glutamicum

<400> SEQUENCE: 2
atgaatagcg taaataattc ctcgcttgtc cggctggatg tcgatttcgg cgactccacc     60
acggatgtca tcaacaacct tgccactgtt attttcgacg ctggccgagc ttcctccgcc    120
gacgcccttg ccaaagacgc gctggatcgt gaagcaaagt ccggcaccgg cgttcctggt    180
caagttgcta tcccccactg ccgttccgaa gccgtatctg tccctacctt gggctttgct    240
cgcctgagca agggtgtgga cttcagcgga cctgatggcg atgccaactt ggtgttcctc    300
attgcagcac ctgctggcgg cggcaaagag cacctgaaga tcctgtccaa gcttgctcgc    360
tccttggtga agaaggattt catcaaggct ctgcaggaag ccaccaccga gcaggaaatc    420
gtcgacgttg tcgatgccgt gctcaaccca gcaccaaaaa ccaccgagcc agctgcagct    480
ccggctgcgg cggcggttgc tgagagtggg gcggcgtcga caagcgttac tcgtatcgtg    540
gcaatcaccg catgcccaac cggtatcgca cacacctaca tggctgcgga ttccctgacg    600
caaaacgcgg aaggccgcga tgatgtggaa ctcgttgtgg agactcaggg ctcttccgct    660
gtcaccccag tcgatccgaa gatcatcgaa gctgccgacg ccgtcatctt cgccaccgac    720
gtgggagtta agaccgcga gcgtttcgct ggcaagccag tcattgaatc cggcgtcaag    780
cgcgcgatca atgagccagc caagatgatc gacgaggcca tcgcagcctc caagaaccca    840
aacgcccgca aggtttccgg ttccggtgtc gcggcatctg ctgaaaccac cggcgagaag    900
ctcggctggg gcaagcgcat ccagcaggca gtcatgaccg cgtgtcccta catggttcca    960
ttcgtagctg ccggcggcct cctgttggct ctcggcttcg cattcggtgg atacgacatg   1020
gcgaacggct ggcaagcaat cgccacccag ttctctctga ccaacctgcc aggcaacacc   1080
gtcgatgttg acggcgtggc catgaccttc gagcgttcag gcttcctgtt gtacttcggc   1140
```

```
gcagtcctgt tcgccaccgg ccaagcagcc atgggcttca tcgtggcagc cctgtctggc    1200
tacaccgcat acgcacttgc tggacgccca ggcatcgcgc cgggcttcgt cggtggcgcc    1260
atctccgtca ccatcggcgc tggcttcatt ggtggtctgg ttaccggtat cttggctggt    1320
ctcattgccc tgtggattgg ctcctggaag gtgccacgcg tggtgcagtc actgatgcct    1380
gtggtcatca tcccgctact tacctcagtg gttgttggtc tcgtcatgta cctcctgctg    1440
ggtcgcccac tcgcatccat catgactggt ttgcaggact ggctatcgtc aatgtccgga    1500
agctccgcca tcttgctggg tatcatcttg ggcctcatga tgtgtttcga cctcggcgga    1560
ccagtaaaca aggcagccta cctctttggt accgcaggcc tgtctaccgg cgaccaagct    1620
tccatggaaa tcatggccgc gatcatggca gctggcatgg tcccaccaat cgcgttgtcc    1680
attgctaccc tgctgcgcaa gaagctgttc accccagcag agcaagaaaa cggcaagtct    1740
tcctggctgc ttggcctggc attcgtctcc gaaggtgcca tcccattcgc cgcagctgac    1800
ccattccgtg tgatcccagc aatgatggct ggcggtgcaa ccactggtgc aatctccatg    1860
gcactgggcg tcggctctcg ggctccacac ggcggtatct tcgtggtctg gcaatcgaa     1920 ccatggtggg gctggctcat cgcacttgca gcaggcacca tcgtgtccac catcgttgtc    1980
atcgcactga agcagttctg ccaaacaag gccgtcgctg cagaagtcgc gaagcaagaa     2040
gcacaacaag cagctgtaaa cgcataa                                       2067

<210> SEQ ID NO 3
<211> LENGTH: 1167
<212> TYPE: DNA
<213> ORGANISM: Streptomyces rubiginosus

<400> SEQUENCE: 3
atgaactacc agcccacccc cgaggacagg ttcaccttcg gactgtggac cgtcggctgg     60
cagggacggg acccccttcgg tgacgccacg cggcgcgccc tcgacccggt cgagtcggtg    120
cggcggctgg ccgagctggg cgcccacggc gtcacgttcc acgacgacga cctcatcccc    180
ttcggctcca gcgacagcga gcgcgaggag cacgtcaagc ggttccggca ggcgctggac    240
gacaccggca tgaaggtgcc gatggccacc accaacctgt tcacccaccc ggtgttcaag    300
gacggcggct tcaccgccaa cgaccgcgac gtgcgccgct acgccctgcg caagaccatc    360
cgcaacatcg acctcgcggt cgagctcggc gccgagacct atgtggcctg ggcggccgc    420 gagggtgccg agtcgggtgg cgccaaggac gtgcgggacg ccctcgaccg catgaaggag    480
gccttcgacc tgctcggcga gtacgtcacc tcccagggct acgacatccg cttcgccatc    540
gagcccaagc cgaacgagcc gcgcggcgac atcctgctcc ccaccgtcgg ccacgccctg    600
gcgttcatcg agcgcctgga gcgaccggag ctgtacggcg tgaacccga  ggtcggccac    660 gagcagatgg ccgggctgaa cttcccgcac ggcatcgcgc aggcgctgtg ggcgggcaag    720
ctgttccaca tcgacctcaa cggccagaac ggcatcaagt acgaccagga cctccgcttc    780
ggcgcgggcg acctgcgggc gcgttctgg ctggtggacc tgctggagtc ggccggctac    840 agcggccccgc ggcacttcga cttcaagccg ccgcggaccg aggacttcga cggggtgtgg    900
gcctcggcgg ccggctgcat gcgcaactac ctgatcctca aggagcgtgc ggcggccttc    960
cgcgccgacc ccgaggtgca ggaggcgctg cgcgcgtccc gtctggacga gctgccccgg   1020
cccacggcgg ccgacggtct gcaggccctg ctcgacacc ggtccgcctt cgaggagttc    1080
gacgtcgacg cggcggcggc ccgtgggatg gccttcgagc gcctggacca gctggcgatg    1140
gaccacctgc tgggcgcccg gggctga                                       1167
```

<210> SEQ ID NO 4
<211> LENGTH: 388
<212> TYPE: PRT
<213> ORGANISM: Streptomyces rubiginosus

<400> SEQUENCE: 4

```
Met Asn Tyr Gln Pro Thr Pro Glu Asp Arg Phe Thr Phe Gly Leu Trp
1               5                   10                  15

Thr Val Gly Trp Gln Gly Arg Asp Pro Phe Gly Asp Ala Thr Arg Arg
            20                  25                  30

Ala Leu Asp Pro Val Glu Ser Val Arg Arg Leu Ala Glu Leu Gly Ala
        35                  40                  45

His Gly Val Thr Phe His Asp Asp Leu Ile Pro Phe Gly Ser Ser
    50                  55                  60

Asp Ser Glu Arg Glu Glu His Val Lys Arg Phe Arg Gln Ala Leu Asp
65                  70                  75                  80

Asp Thr Gly Met Lys Val Pro Met Ala Thr Thr Asn Leu Phe Thr His
                85                  90                  95

Pro Val Phe Lys Asp Gly Gly Phe Thr Ala Asn Asp Arg Asp Val Arg
            100                 105                 110

Arg Tyr Ala Leu Arg Lys Thr Ile Arg Asn Ile Asp Leu Ala Val Glu
        115                 120                 125

Leu Gly Ala Glu Thr Tyr Val Ala Trp Gly Gly Arg Glu Gly Ala Glu
    130                 135                 140

Ser Gly Gly Ala Lys Asp Val Arg Asp Ala Leu Asp Arg Met Lys Glu
145                 150                 155                 160

Ala Phe Asp Leu Leu Gly Glu Tyr Val Thr Ser Gln Gly Tyr Asp Ile
                165                 170                 175

Arg Phe Ala Ile Glu Pro Lys Pro Asn Glu Pro Arg Gly Asp Ile Leu
            180                 185                 190

Leu Pro Thr Val Gly His Ala Leu Ala Phe Ile Glu Arg Leu Glu Arg
        195                 200                 205

Pro Glu Leu Tyr Gly Val Asn Pro Glu Val Gly His Glu Gln Met Ala
    210                 215                 220

Gly Leu Asn Phe Pro His Gly Ile Ala Gln Ala Leu Trp Ala Gly Lys
225                 230                 235                 240

Leu Phe His Ile Asp Leu Asn Gly Gln Asn Gly Ile Lys Tyr Asp Gln
                245                 250                 255

Asp Leu Arg Phe Gly Ala Gly Asp Leu Arg Ala Ala Phe Trp Leu Val
            260                 265                 270

Asp Leu Leu Glu Ser Ala Gly Tyr Ser Gly Pro Arg His Phe Asp Phe
        275                 280                 285

Lys Pro Pro Arg Thr Glu Asp Phe Asp Gly Val Trp Ala Ser Ala Ala
    290                 295                 300

Gly Cys Met Arg Asn Tyr Leu Ile Leu Lys Glu Arg Ala Ala Ala Phe
305                 310                 315                 320

Arg Ala Asp Pro Glu Val Gln Glu Ala Leu Arg Ala Ser Arg Leu Asp
                325                 330                 335

Glu Leu Ala Arg Pro Thr Ala Ala Asp Gly Leu Gln Ala Leu Leu Asp
            340                 345                 350

Asp Arg Ser Ala Phe Glu Glu Phe Asp Val Asp Ala Ala Ala Ala Arg
        355                 360                 365

Gly Met Ala Phe Glu Arg Leu Asp Gln Leu Ala Met Asp His Leu Leu
    370                 375                 380
```

```
Gly Ala Arg Gly
385

<210> SEQ ID NO 5
<211> LENGTH: 323
<212> TYPE: PRT
<213> ORGANISM: Corynebacterium glutamicum

<400> SEQUENCE: 5

Met Pro Gln Lys Pro Ala Ser Phe Ala Val Gly Phe Asp Ile Gly Gly
1               5                   10                  15

Thr Asn Met Arg Ala Gly Leu Val Asp Glu Ser Gly Arg Ile Val Thr
            20                  25                  30

Ser Leu Ser Ala Pro Ser Pro Arg Thr Thr Gln Ala Met Glu Gln Gly
        35                  40                  45

Ile Phe Asp Leu Val Glu Gln Leu Lys Ala Glu Tyr Pro Val Gly Ala
    50                  55                  60

Val Gly Leu Ala Val Ala Gly Phe Leu Asp Pro Glu Cys Glu Val Val
65                  70                  75                  80

Arg Phe Ala Pro His Leu Pro Trp Arg Asp Glu Pro Val Arg Glu Lys
                85                  90                  95

Leu Glu Asn Leu Leu Gly Leu Pro Val Arg Leu Glu His Asp Ala Asn
            100                 105                 110

Ser Ala Ala Trp Gly Glu His Arg Phe Gly Ala Ala Gln Gly Ala Asp
        115                 120                 125

Asn Trp Val Leu Leu Ala Leu Gly Thr Gly Ile Gly Ala Ala Leu Ile
    130                 135                 140

Glu Lys Gly Glu Ile Tyr Arg Gly Ala Tyr Gly Thr Ala Pro Glu Phe
145                 150                 155                 160

Gly His Leu Arg Val Val Arg Gly Gly Arg Ala Cys Ala Cys Gly Lys
                165                 170                 175

Glu Gly Cys Leu Glu Arg Tyr Cys Ser Gly Thr Ala Leu Val Tyr Thr
            180                 185                 190

Ala Arg Glu Leu Ala Ser His Gly Ser Phe Arg Asn Ser Gly Leu Phe
        195                 200                 205

Asp Lys Ile Lys Ala Asp Pro Asn Ser Ile Asn Gly Lys Thr Ile Thr
    210                 215                 220

Ala Ala Ala Arg Gln Glu Asp Pro Leu Ala Leu Ala Val Leu Glu Asp
225                 230                 235                 240

Phe Ser Glu Trp Leu Gly Glu Thr Leu Ala Ile Ile Ala Asp Val Leu
                245                 250                 255

Asp Pro Gly Met Ile Ile Ile Gly Gly Gly Leu Ser Asn Ala Ala Asp
            260                 265                 270

Leu Tyr Leu Asp Arg Ser Val Asn His Tyr Ser Thr Arg Ile Val Gly
        275                 280                 285

Ala Gly Tyr Arg Pro Leu Ala Arg Val Ala Thr Ala Gln Leu Gly Ala
    290                 295                 300

Asp Ala Gly Met Ile Gly Val Ala Asp Leu Ala Arg Arg Ser Val Val
305                 310                 315                 320

Glu Ala Asn

<210> SEQ ID NO 6
<211> LENGTH: 972
<212> TYPE: DNA
<213> ORGANISM: Corynebacterium glutamicum

<400> SEQUENCE: 6
```

-continued

```
atgccacaaa aaccggccag tttcgcggtg ggctttgaca tcggcggcac caacatgcga      60
gccgggcttg tcgacgaatc cgggcgcatc gtgaccagtt tgtcggcgcc gtcgccgcgc     120
acgacgcagg caatggaaca ggggatttt  gatctagtcg aacagctcaa ggccgaatac     180
ccggttggtg ctgtgggact tgccgtcgcg ggattttgg  atcctgagtg cgaggttgtt     240
cgatttgccc cgcaccttcc ttggcgcgat gagccagtgc gtgaaaagtt ggaaaacctt     300
ttgggcctgc ctgttcgttt ggaacatgat gccaactcag cagcgtgggg tgagcatcgt     360
tttggtgcag ctcaaggcgc tgacaactgg gttttgttgg cactcggcac tggaattggt     420
gcagcgctga ttgaaaaagg cgaaatttac cgtggtgcat atggcacggc accagaattt     480
ggtcatttgc gtgttgttcg tggcggacgc gcatgtgcgt gtggcaaaga aggctgcctg     540
gagcgttact gttccggtac tgccttggtt tacactgcgc gtgaattggc ttcgcatggc     600
tcattccgca acagcgggct gtttgacaag atcaaagccg atccgaattc catcaatgga     660
aaaacgatca ctgcggcagc gcgccaagaa gacccacttg ctctcgccgt tctggaagat     720
ttcagcgagt ggctgggcga aactttggcg atcattgctg atgtccttga cccaggcatg     780
atcatcattg gtggcggact gtccaatgct gccgaccttt atttggatcg ctcggtcaac     840
cactattcca cccgcatcgt cggcgcagga tatcgccctt tggcacgcgt tgccacagct     900
cagttgggtg cggatgctgg catgatcggt gtcgctgatc tagctcgacg ctctgtagtg     960
gaagccaact ag                                                         972

<210> SEQ ID NO 7
<211> LENGTH: 28
<212> TYPE: DNA
<213> ORGANISM: Artificial sequence
<220> FEATURE:
<223> OTHER INFORMATION: primer

<400> SEQUENCE: 7
gcaagcttcc atcgcagcct ccaagaac                                         28

<210> SEQ ID NO 8
<211> LENGTH: 28
<212> TYPE: DNA
<213> ORGANISM: Artificial Sequence
<220> FEATURE:
<223> OTHER INFORMATION: PCR Primer

<400> SEQUENCE: 8
gcaagcttcg gagcttccgg acattgac                                         28

<210> SEQ ID NO 9
<211> LENGTH: 95
<212> TYPE: DNA
<213> ORGANISM: Artificial sequence
<220> FEATURE:
<223> OTHER INFORMATION: PCR Primer

<400> SEQUENCE: 9
attgacaatt aatcatcggc tcgtataatg tgtggaattg tgagcggata acaatttcac      60
acaggaaaca gctatgaact accagcccac ccccg                                 95

<210> SEQ ID NO 10
<211> LENGTH: 19
<212> TYPE: DNA
<213> ORGANISM: Artificial Sequence
<220> FEATURE:
<223> OTHER INFORMATION: PCR Primer
```

-continued

```
<400> SEQUENCE: 10
tcagccccgg gcgcccagc                                                   19

<210> SEQ ID NO 11
<211> LENGTH: 38
<212> TYPE: DNA
<213> ORGANISM: Artificial Sequence
<220> FEATURE:
<223> OTHER INFORMATION: PCR Primer

<400> SEQUENCE: 11
gaacgcgagg gggcactctt atgccacaaa aaccggcc                              38

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12
ctagttggct tccactacag agcg                                             24
```

PRODUCTION OF AMINO ACIDS FROM SUCROSE IN *CORYNEBACTERIUM GLUTAMICUM*

CROSS-REFERENCE TO RELATED APPLICATIONS

This application claims priority to U.S. Provisional Patent Application No. 60/955,348, filed on Sep. 26, 2007. That application is incorporated by reference as if fully rewritten herein.

BACKGROUND OF THE INVENTION

1. Field of the Invention

The present invention relates generally to methods and compositions for production of amino acids by bacteria of the genus *Corynebacterium* or *Brevibacterium* using sucrose as a carbon source. More particularly, the invention relates to the production of L-lysine from *Corynebacterium glutamicum* using sucrose as a carbon source.

2. Related Art

Many commercial fermentations of *Corynebacterium* and *Brevibacterium* use glucose as a carbon source. Consequently, many bacterial production cultures have been designed to optimize rates of production and/or yields using glucose as a carbon source. Production of the commercially important amino acid L-lysine was been a particular target of optimization.

Because of cost and other possible considerations, use of alternative, non-glucose carbon sources may be preferred in some parts of the world. One possible non-glucose carbon source is sucrose. Sucrose may be obtained, for example, from sugar cane or sugar beet. Unfortunately, because microorganisms often transport and utilize sucrose differently than glucose, production of a desired amino acid or fine chemical product from many microorganisms using sucrose as a carbon source can suffer from reduced efficiency. This may particularly be the case where the microorganisms using sucrose as a carbon source have been designed for optimal growth on glucose. That is the case for *Corynebacterium glutamicum*, one of the microorganisms most commonly used for the manufacture of amino acids such L-lysine by fermentation.

A metabolic pathway for utilization of sucrose in *C. glutamicum* was suggested by Wittmann, et al., "Metabolic Fluxes in *Corynebacterium glutamicum* during Lysine Production with Sucrose as Carbon Source," *Appl. & Enviro. Microbiol.* 70(12): 7277-7287 (2004). Wittmann, et al., hypothesized that *Corynebacterium glutamicum* has a sucrose uptake mechanism that occurs by a phosphotransferase system (PTS), in which sucrose is phosphorylated at the glucose ring and subsequently hydrolyzed in the cell to glucose-6-phosphate and fructose. The PTS in *C. glutamicum* is a general carbohydrate transfer system that utilizes of a combination of two commonly shared cytoplasmic proteins designated enzyme I and Hpr, encoded by the ptsI and ptsH genes respectively, that interact with a discrete set of membrane bound EII proteins complexes designated fructose-pts, sucrose-pts, and glucose-pts encoded by the ptsF, ptsS, and ptsG genes respectively, that preferentially transport fructose, sucrose and glucose, respectively (Tanaka et al, *Microbiology* (2008) 154, 264-274). There are also two pts genes designated HCg12933 and NCg12934 that encode proteins with unknown specificities (id.).

Wittmann, et al., also suggested that following the hydrolysis, the resulting fructose is excreted from the cell, then reimported through the fructose-PTS uptake system and the mannose PTS uptake system (the latter now believed to be the same as the glucose-PTS). The existence of multiple uptake systems for sucrose (sucrose-PTS, fructose-PTS, and glucose-PTS) and therefore multiple entry points for carbon into the cell has been hypothesized as a possible reason for unfavorable performance on sucrose.

During lysine production on glucose, about 65% of the carbon goes down the pentose phosphate pathway (PPP) for the production of NADPH, which is used in lysine synthesis. During lysine synthesis on sucrose, however, it is believed that a much lower percentage of carbon goes down the PPP, because slightly less than half of the total carbon enters glycolysis as fructose-1,6-phosphate.

As illustrated in FIG. 1, when a wild type *C. glutamicum* is grown on sucrose, it is believed that about 90% of the fructose that would enter the *C. glutamicum* cell enters through the fructose-PTS as fructose-1-phosphate. The fructose-1-phosphate is phosphorylated to make fructose-1,6-phosphate. It is believed that fructose-1,6-phosphate does not go through the PPP pathway, in large part because 6-phosphofructokinase is largely an irreversible enzyme and there is very little fructose-1,6-biphosphatase activity in *C. glutamicum* grown on sucrose. Fructose-1,6-diphosphate will therefore preferentially enter glycolysis and the TCA cycle, which does not provide reducing power for commercial level lysine synthesis.

About 10% of fructose entering *C. glutamicum* is believed to be taken up by the glucose-PTS system as fructose-6-phosphate. Fructose-6-phosphate may contribute to the amount of carbon directed to PPP flux by action of glucose-6-phosphate isomerase operating in the gluconeogenetic direction to produce glucose-6-phosphate from fructose-6-phosphate. One proposed metabolic pathway for sucrose utilization in *Corynebacterium* including routes through glycolysis and the PPP shunt is shown in FIG. 1.

Increased lysine production from *Corynebacterium* on sucrose has been evaluated. One method that might be used to increase production was set forth by Georgi, et al., "Lysine and Glutamate Production by *Corynebacterium glutamicum* on Glucose, Fructose, and Sucrose: Roles of Malic Enzyme and Fructose-1,6-bisphosphatase," *Metabolic Eng.* 7:291-301 (2005).

The Georgi, et al., strategy purportedly involves use of a constitutive promoter to overexpress the fructose-1,6-bisphosphatase gene fbp. This strategy may be unfavorable, however, because it may result in the creation of strains of *Corynebacterium* that, while optimized for growth on sucrose, have characteristics that could lead to suboptimal growth on glucose. This may potentially reduce the flexibility of the economically viable uses of the strains, which may not perform in a way that allows use of either sucrose or glucose as a carbon source, depending on what is economically advantageous as conditions change.

Another purported strategy for increasing lysine production from *Corynebacterium* on sucrose is reported in WO2005/059139A2, as well as Becker, et al., "Amplified Expression of Fructose 1,6-bisphosphatase in *Corynebacterium glutamicum* increases in vivo flux through the pentose of phosphates pathway and of lysine production on different carbon sources," *Appl. Envir. Microbiol.* 71: 8587-8596 (2005). In this strategy, fructose-1,6-bisphosphatase is overexpressed. This purportedly allows fructose-1,6-P to return to the PPP, eventually increasing the amount of NADPH. The basic strategy of Georgi, et al. and Becker, et al. is illustrated in FIG. 5.

A further proposal for possibly increasing lysine production from *Corynebacterium* using sucrose as a carbon source was reported in Moon, et al., "Analyses of enzyme II gene mutants for sugar transport and heterologous expression of fructokinase gene in *Corynebacterium glutamicum* ATCC 13032" *FEMS Microbiol. Lett.* 244: 259-266 (2005). Moon demonstrated that expression of a *Clostridium acetoybutylicum* fructose kinase gene in *C. glutamicum* reduced the fructose exported into the media from the transformed strain during growth on sucrose which was otherwise exported during log phase growth of the parent strain lacking the fructokinase activity. Moon, et al. also demonstrated that a ptsF mutant strain lacking fructose-pts activity but expressing the fructokinse enzyme was able to grow to a higher optical density and utilize exported fructose better than the mutant strain lacking the fructokinase activity. It was hypothesized that expression of fructokinase in *C. glutamicum* would allow the conversion of fructose- to fructose 6-P which would then proceed to the PPP shunt possibly increasing lysine production, instead of being exported from the cell and then re-imported via the PTS system predominantly as fructose 1-phosphate. The scheme hypothesized by Moon, et al. is illustrated in FIG. 6.

The kinetics of lysine production with fructose and sucrose as carbon sources is reported in Kiefer, et al., "Influence of glucose, fructose and sucrose as carbon sources on kinetics and stoichiometry of lysine production by *Corynebacterium glutamicum*," *J. Indus. Microbiol. & Biotech.* 28: 338-343 (2002); and Kiefer, et al., "Comparative Metabolic Flux Analysis of Lysine-Producing *Corynebacterium glutamicum* Cultured on Glucose or Fructose," *Appl. & Envir. Microbiol.* 70(1): 229-239 (2004). The inclusion of the *E. coli* xylose isomerase gene in an altered *Corynebacterium* cell is reported in Kawaguchi, et al., "Engineering of a Xylose Metabolic Pathway in *Corynebacterium glutamicum*," *Appl. & Envir. Microbiol.* 72(5): 3418-3428 (2006)

It would be desirable to create a strain of microorganism that is optimized for growth on sucrose but that retains characteristics favorable for growth on glucose. Such a strain could result in fermentative production of amino acids from sucrose being more economically favorable when sucrose is available; when sucrose is unavailable or is not as plentiful or inexpensive as glucose, such a strain could efficiently be used for fermentative production of amino acids from glucose. It is an object of the invention to create such a strain. It is also an object of the invention to produce lysine using strains produced by embodiments of the invention. Preferably, the amount and/or rate of lysine production will be greater in bacteria produced in embodiments of the invention. Of course, the invention as defined by the claims shall not be limited by its ability to satisfy one or more of the objects of the invention.

BRIEF SUMMARY OF THE INVENTION

The present invention relates to the production of amino acids by bacteria of the genus *Corynebacterium* or *Brevibacterium* using sucrose as a carbon source. In one aspect, the invention provides novel strains of microorganisms that have attenuated or blocked fructose transport mechanisms and methods for making the same. In another aspect, there are provided methods of fermentation using enzymes in the media that exploit the natural features of the endogenous PTS of *C. glutamicum* for optimal growth on sucrose.

In one embodiment microorganisms may be fermented in a fermentation broth to which glucose isomerase and/or invertase have been added. In another embodiment, glucose isomerase and/or invertase may also be expressed in the cell and exported into the media. In a different aspect, microorganisms of the invention are mutated to have attenuated or blocked fructose transport or fructose export mechanisms. In yet another aspect, the microorganisms may be engineered to express glucose isomeraase and glucokinase in the cytoplasm to drive imported fructose toward the PPP shunt via formation of glucose-6-phosphate. Methods of producing amino acids using these microorganisms, media, or both, are also included aspects of the invention.

BRIEF DESCRIPTION OF THE DRAWINGS/FIGURES

FIG. 1 depicts wild type metabolism of sucrose and fructose in *Corynebacterium*.

FIG. 2 depicts a sucrose and fructose metabolism pathway of *Corynebacterium* according to an embodiment of the invention providing a fructose-PTS knockout mutant such as described by Moon, et al., "Analyses of enzyme II gene mutants for sugar transport and heterologous expression of fructokinase gene in *Corynebacterium glutamicum* ATCC 13032" *FEMS Microbiol. Lett.* 244: 259-266 (2005). A Moon et al type PTS knockout mutant is used in the present invention in conjunction with the addition or secretion of glucose isomerase in the fermentation media.

Figure 5:
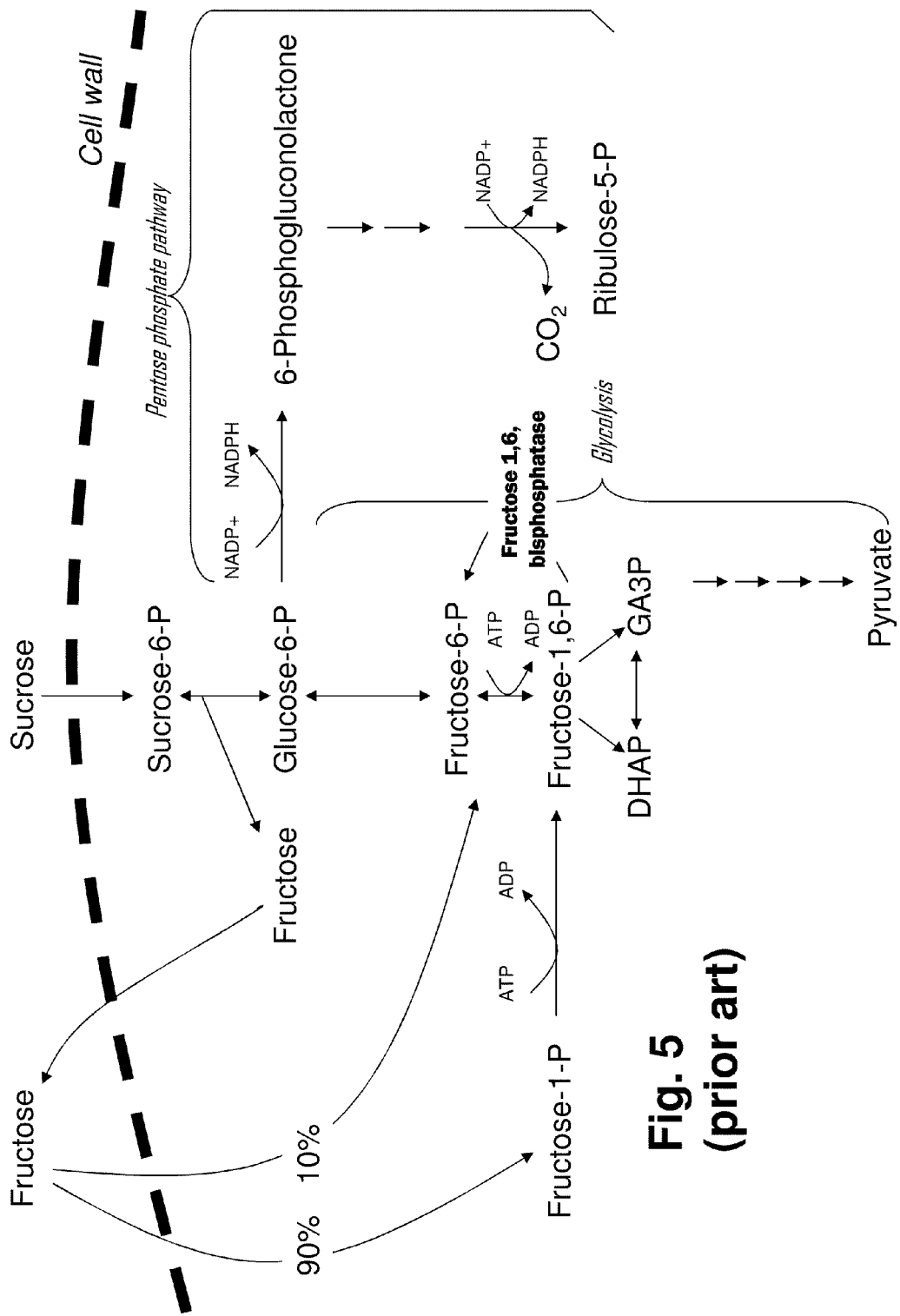

FIG. 5 depicts a sucrose and fructose metabolism pathway of the prior art, where *Corynebacterium* in which fructose-1, 6-bisphosphate has been overexpressed. This pathway is reported in WO2005/059139A2, as well as Becker, et al., "Amplified Expression OF Fructose 1,6-bisphosphatase in *C. glutamicum* increases in vivo flux through the pentose of phosphates pathway and of lysine production on different carbon sources," *Appl. Envir. Microbiol.* 71: 8587-8596 (2005).

Figure 6:
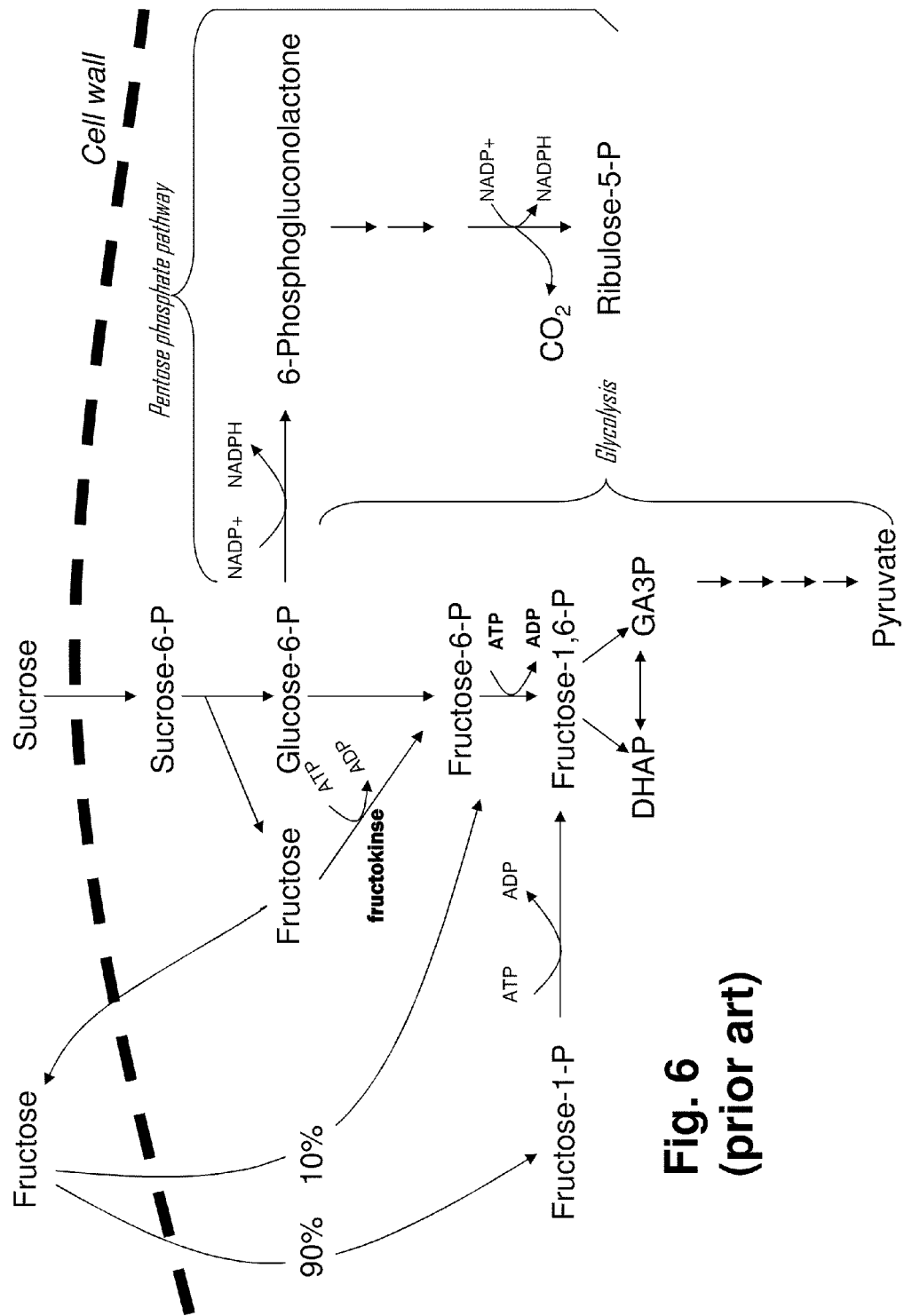

FIG. 6 depicts a sucrose and fructose metabolism pathway of *Corynebacterium* of the prior art according to Moon et al., in which a fructose kinase is also expressed.

DETAILED DESCRIPTION OF THE INVENTION

The foregoing Background and Summary as well as the detailed description that follows contains citations to various references that may aid one of ordinary skill in the art better understand the present invention and/or that provide descriptions of compositions, bacterial strains and methods of making *C. glutamicum* mutants, and genetically engineered expression vectors that will readily enable one of ordinary skill in the art to practice the inventions set forth herein. Accordingly, rather than reproduce the salient descriptions from numerous references known in the art, every reference cited herein is hereby incorporated by reference to the extent that such references teach the availability of strains, methods of making mutant and recombinants, the properties and availability of strains and processes of fermentation of *C. glutamicum* to produce lysine and other amino acids. To the extent any teaching of an incorporated reference conflicts with the description provided herein, this description controls The present invention relates to the production of fine chemicals by bacteria of the genus *Corynebacterium* or *Brevibacterium* using sucrose as a carbon source. These fine chemicals may be, for example, amino acids or vitamins. The amino acids that may be produced include, for example, but are not limited to L-lysine, L-tryptophan, L-methionine, L-threonine, and homoserine.

It has been determined herein that increased amounts of NADPH in a bacterial cell increase product yield, specifically in anabolic processes where NADPH is a limiting factor. A way of carrying chemical energy from reactions of catabolism to the energy-requiring reactions of biosynthesis, such as the formation of amino acids, is in the form of hydrogen atoms or electrons.

To be effective as reducing agents, hydrogen atoms must have considerable free energy. Such high-energy hydrogen atoms are obtained from cell fuels by dehydrogenases, which catalyze removal of hydrogen atoms from fuel molecules and their transfer to specific coenzymes, particularly to the oxidized form of nicotinamide adenine dinucleotide phosphate ($NADP^+$). The reduced, or hydrogen-carrying, form of this coenzyme, designated NADPH, is a carrier of energy-rich electrons from catabolic reactions to electron-requiring biosynthetic reactions.

Preferably, NADPH availability is increased by increasing the carbon flux through the oxidative branch of the pentose phosphate pathway. Theoretically, 12 NADPH's are generated per glucose when glucose is exclusively metabolized in the pentose phosphate pathway, but only two NADPH's are produced per glucose metabolized in the TCA cycle (tricarboxylic acid, also called the citric acid cycle). Ishino, S. et al., J. Gen. Appl. Microbiol. 37:157-165 (1991). The present invention provides a method of producing L-amino acids by culturing an altered bacterial cell which has an increase in the carbon flux of sucrose and sucrose products through the pentose phosphate pathway.

The pentose phosphate pathway ("PPP"), also called the hexose monophosphate shunt, is an alternative route for glucose catabolism. The pentose phosphate pathway produces NADPH and under lysine fermentation conditions is more active. Ishino, S. et al., J. Gen. Appl. Microbiol. 37:157-165 (1991). Because less sucrose is naturally sent through the PPP, comparatively less NADPH is formed from sucrose. The PPP is further discussed in U.S. Pat. No. 6,830,903, to O'Donohue, et al.

In one aspect, the invention provides a novel strain or strains of microorganisms that have increased amounts of NADPH as a result of an attenuated or blocked fructose uptake mechanism. Such an attenuation or blockage may be accomplished, for example, by disruption or removal of a gene encoding an enzyme in the fructose-PTS uptake pathway. Such an enzyme may be, for example, fructose-PTS enzyme II (SEQ ID NO: 1), encoded by the ptsF gene (SEQ. ID. NO: 2). An example of disruption of the ptsF is set forth in Example 1, below. Those skilled in the art may recognize that other genes may also be effectively disrupted or attenuated to reduce or eliminate fructose uptake.

Figure 1:
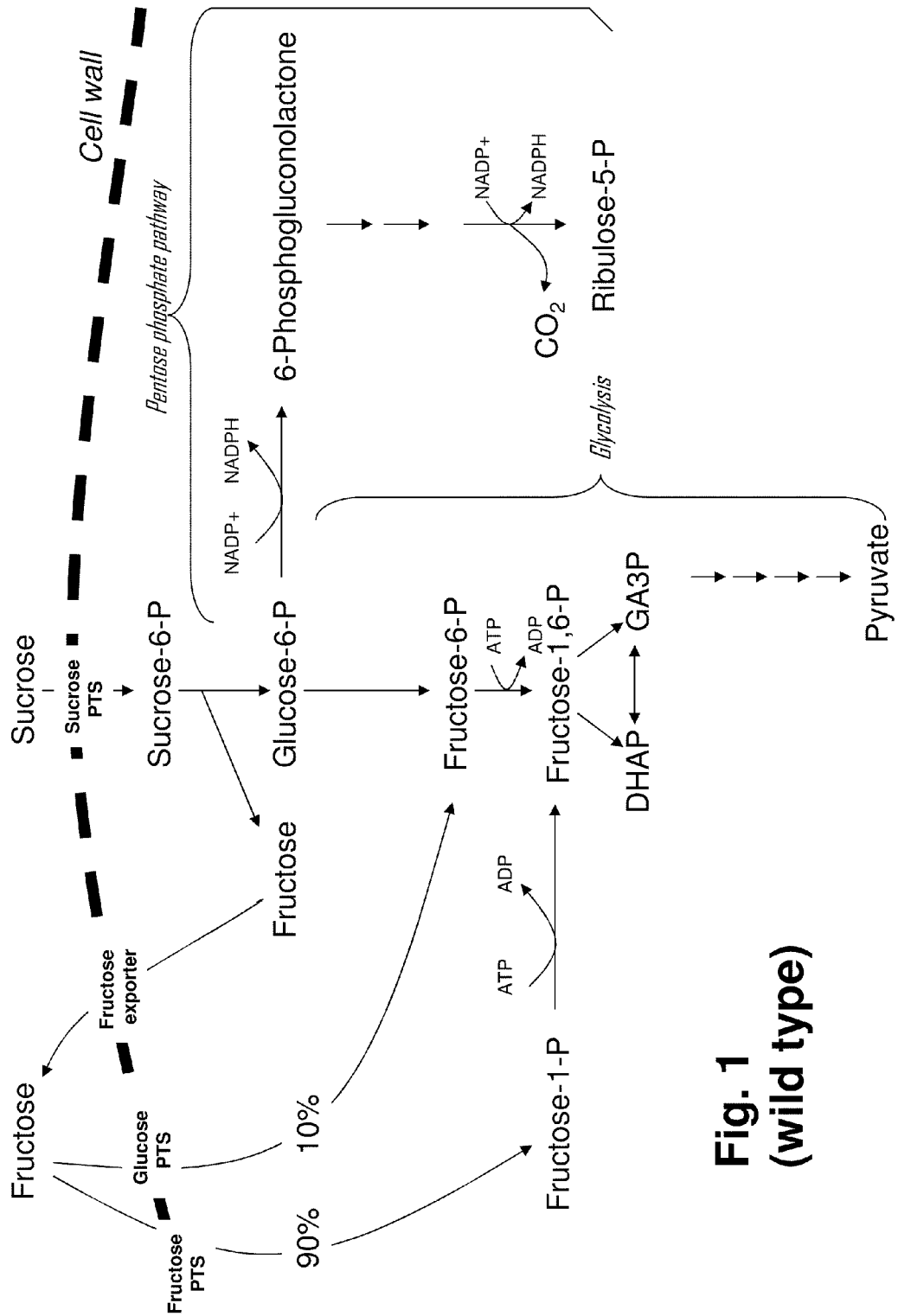
Figure 2:
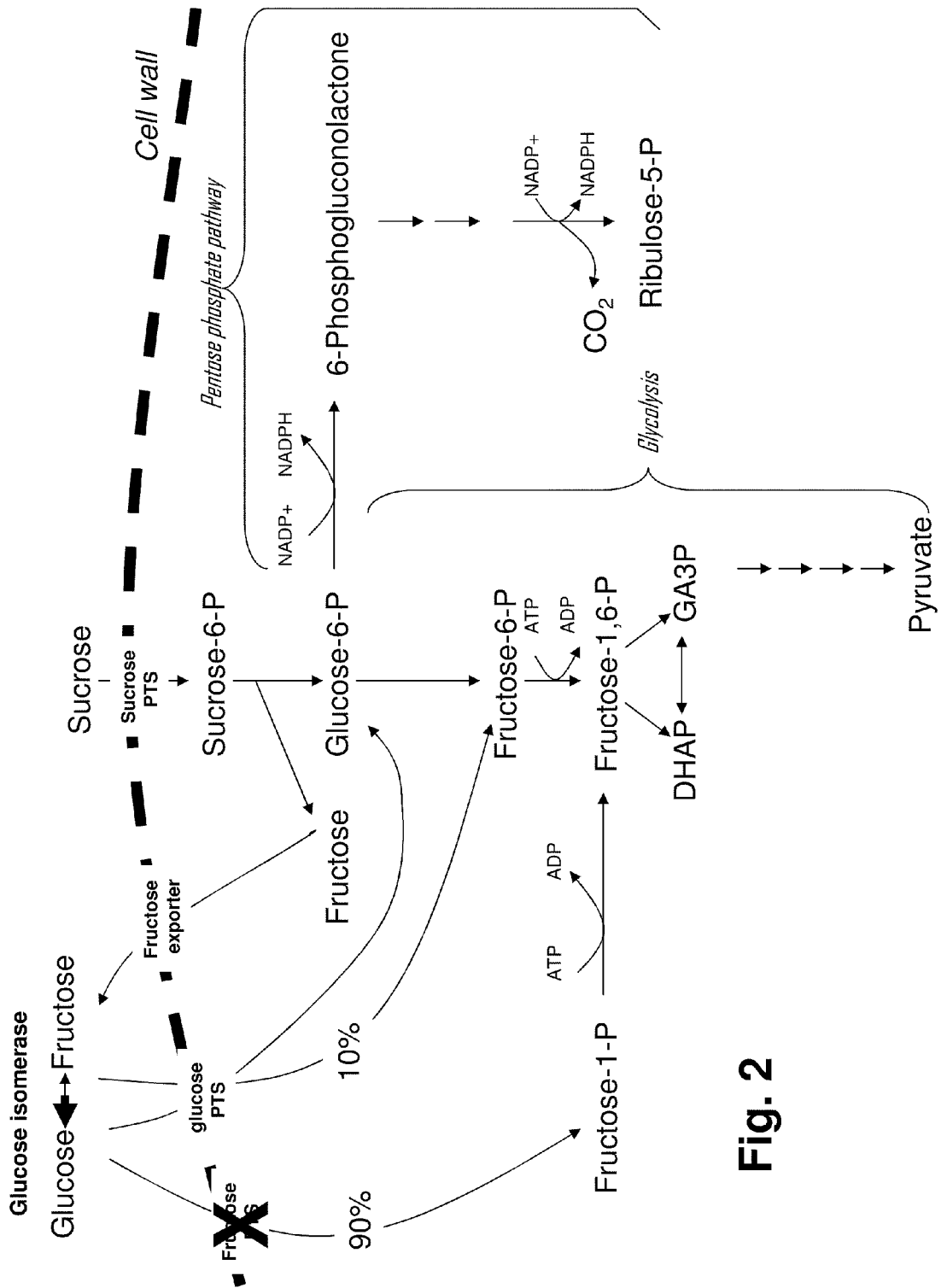

Reduction or elimination of fructose uptake in a microorganism grown on sucrose such as by use of a fructose-PTS enzyme mutant, for example as described by Moon et al, will necessarily result in the accumulation of fructose in the medium because fructose derived from sucrose uptake is first exported by an export mechanism before reentering the cell. This fructose can be converted to glucose by operation of glucose isomerase. This glucose will then be efficiently taken up by the glucose phosphotransferase system (glucose-PTS) and converted to glucose-6-phosphate which readily enters the PPP shunt rather than proceeding preferentially through glycolysis such as occurs when fructose, which would otherwise preferentially enter the cell via the fructose-PTS enzyme, is first converted to fructose-1-phosphate. Because the glucose is much more efficiently transferred into the cell by the glucose-PTS than fructose, the equilibrium of isomerization will be driven toward converting the exported fructose into glucose. A proposed metabolic pathway for sucrose utilization in this embodiment of the invention is shown in FIG. 2.

In this aspect of the invention, glucose isomerase is included in the media. Inclusion of glucose isomerase in the media may, for example, be accomplished through addition of the enzyme prior to the beginning of fermentation, through addition of the enzyme during the fermentation, or through continuous addition of the enzyme as necessary. Glucose isomerase may be added as a liquid enzyme, and immobilized enzyme, or a mixture of the two. In a preferred embodiment of the invention, sufficient glucose isomerase is added to maintain an equilibrium of conversion of fructose to glucose. Glucose isomerase is commonly used in the commercial manufacture of high fructose corn syrup from dextrose, and is readily available in industrial quantities from commercial manufacturers such as Genecor, a division of Danisco US, (Rochester, N.Y.).

In another embodiment of this aspect, the microorganism may include a gene that is transcribed to produce glucose isomerase that is exported into the media. This could replace or supplement addition of glucose isomerase to the medium, as described above. For example, a gene for glucose isomerase (SEQ ID NO: 3) (E.C. 5.3.1.5 D-xylose ketol-isomerase) may be cloned from an organism such as *Streptomyces rubiginosus* and expressed in a strain of *C. glutamicum*. One example of a glucose isomerase is shown in SEQ ID NO: 4. Genes encoding glucose isomerase in other organisms may also be used; for example, a gene could be obtained from a strain of *Brevibacterium*. Vectors containing promoters for expression of recombinant genes in *C. glutamicum* are well known in the art, as are vectors containing signal sequences needed to make a fusion protein that will be exported into the media, for example, the vectors and signal sequences for PS2 protein of the csoB gene of *C. glutamicum* described for example by Tateno et al, *Applied Microbiology and Biotechnology*, (2007) 77: 533-541 and Salim et al, Appl. Environ. Microbiol., (1997) 63: 4392-4400.

Figure 3:
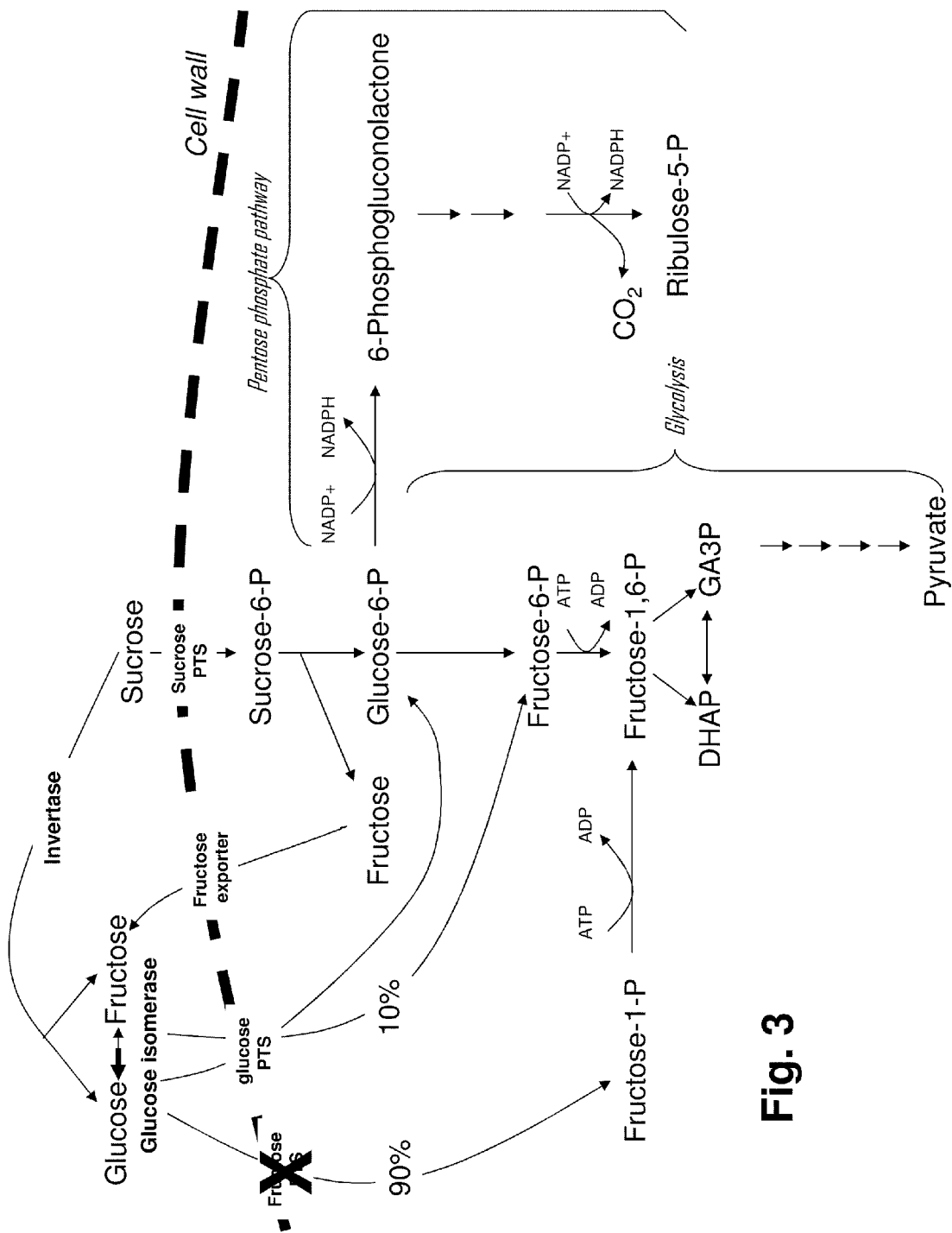
FIG. 3 depicts a sucrose and fructose metabolism pathway of *Corynebacterium* according to an embodiment of the invention in which invertase and glucose isomerase are added or secreted into the fermentation medium in conjunction with a fructose-PTS knockout mutant such as described by Moon et al.

In another embodiment, the invention includes the addition of the enzyme invertase to the culture media in addition to glucose isomerase in growth of a *C. glutamicum* having a knock-out mutation in the fructose-PTS enzyme as described above. A proposed metabolic pathway for this embodiment is shown in FIG. 3. Addition of invertase would form glucose and fructose directly from at least a portion of the sucrose carbon supply, further increasing the amount of fructose outside the cell that is available for conversion to glucose by glucose isomerase. This embodiment capitalizes on use of both the glucose-PTS enzyme and the sucrose-PTS enzyme to continue to drive the production of glucose-phosphate in the cell while simultaneously avoiding the production of fructose-1-phosphate by the fructose-PTS. Commercial quantities of invertase are readily available from manufacturers such as Novozymes North America, (Franklinton, N.C.).

Figure 4:
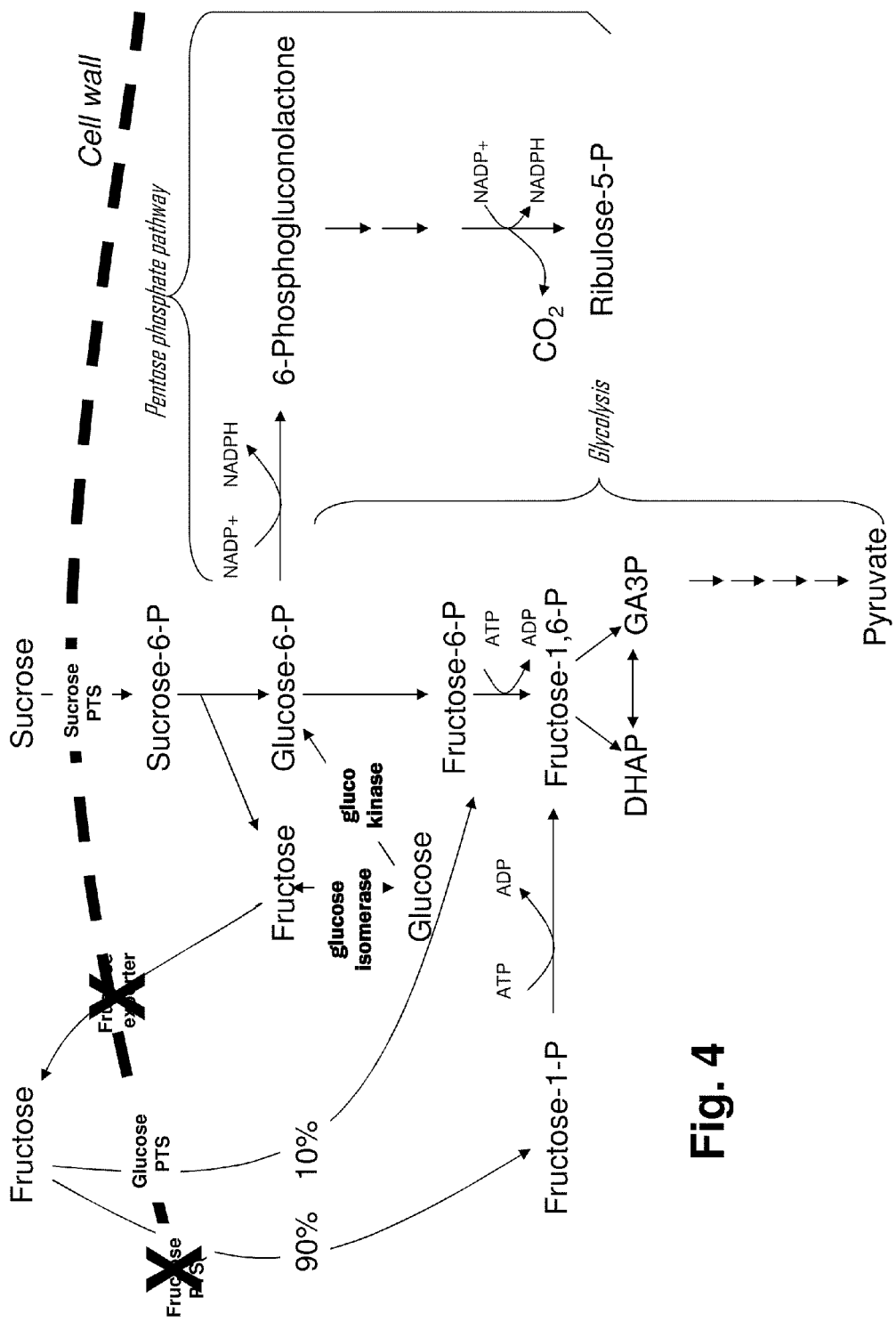
FIG. 4 depicts a sucrose and fructose metabolism pathway of *Corynebacterium* in which glucose isomerase is cloned and expressed inside a mutant cell having both a fructose-PTS knock-out and knock out of the fructose exporter.

In yet another aspect, the invention provides for a dual mutation in both the fructose-PTS enzyme and the fructose exporter responsible for export of fructose from *C. glutamicum* cells grown on sucrose so the activity of the exporter is eliminated or reduced. Embodiments of this aspect may further include increased intracellular expression of glucose isomerase and glucokinase so that the fructose that is retained in the cell is rapidly converted to glucose and then to glucose-6-phosphate. One example of a glucokinase is the glucose kinase according to SEQ ID NO: 5. One glk gene, which codes for glucose kinase in *C. glutamicum*, (SEQ ID NO: 6) is reported by Park, et al., "Characterization of glk, a gene coding for glucose kinase of *C. glutamicum*," *FEMS Microbiol. Lett.* 188: 209-215 (2000). Embodiments that overexpress glucokinase are especially beneficial if the strain does not otherwise have sufficient endogenous glucokinase activity to convert the excess glucose formed from retained fructose by the glucose isomerase for ultimate conversion into glucose-6-phosphate. A metabolic pathway for sucrose utilization in this embodiment is shown in FIG. 4.

While the identity of the fructose exporter is not known, its existence is recognized by the observed export of fructose that occurs when *C. glutamicum* cells are grown with sucrose as a carbon source as reported by Moon et al. Thus beginning with a strain carrying the fructose-PTS mutation, such as the ptsF mutant described by Moon et al, the strain is subjected to conventional random mutagenesis by chemical means or otherwise and cells that are capable of growing on sucrose but that do not export fructose are selected. One method of selecting a cell that does not transport fructose is described by Dominguez et al, "New and simple plate test for screening relative transfructosylation activity of fungi," *Rev Iberoam Microl* (2006) 23: 189-191. Dominguez et al, teach an assay whereby cells that have transfructosylation activity can be identified by blue halos around cell colonies grown on agar media. Accordingly, a ptsF mutant of *C. glutamicum* would produce such a blue halo when grown on sucrose minimal media, but mutants lacking the fructose exporter activity would have no halos, making selection of such mutant a mere matter of visual screening of a chemically mutagenized population of *C. glutamicum*. In addition, one of ordinary skill in the art will recognize multiple assays that may be used to detect the concentration of fructose and/or glucose in the fermentation media. For example, high pressure liquid chromatography (HPLC) may be used or conventional colorometric assays may be used, for example, in kits supplied from R-Biopharm AG.

The following examples are provided as a general guide for practicing various aspects of the invention and are not intended to be limiting.

EXAMPLES

Example 1

Example 1 discloses a disruption of fructose-PTS enzyme II (SEQ ID NO: 1), encoded by the ptsF gene (SEQ ID NO:2). This results in increased fructose concentration in the growth medium for a culture grown on sucrose. The process will produce a ptsF mutant analogous to that described by Moon et al.

The following primers are used to amplify a 690 base pair internal region of the *C. glutamicum* ptsF gene. The primers are:

ptsff
5' GCAAGCTTCCATCGCAGCCTCCAAGAAC 3' (SEQ ID NO: 7)

ptsfr
5' GCAAGCTTCGGAGCTTCCGGACATTGAC 3' (SEQ ID NO: 8)

The PCR amplification conditions are employed as follows. The final volume of the PCR reaction is 100 µl. 100 ng of each primer is used along with 50 ng of high molecular weight DNA and 2.5 units of Taq polymerase. Reaction buffer is included at the concentration recommended by the manufacturer, and dNTP's are also included at a final concentration of 200 µM Cycling parameters such as the following are used: 94° C. for 1 minute, followed by 94° C. for 30 seconds, 58° C. for 30 seconds, and 72° C. for 1 minute (30 cycles), 72° C. for 7 minutes followed by 4° C. The PCR fragment is digested with HindIII and cloned into the suicide vector pBGS131 with a kanamyacin resistance gene and the resulting clone is used to transform *C. glutamicum* (NRRL 11474). Integrants are selected for on culture media plates containing 10 µg/ml kanamycin. The knockout of the fructose-PTS system are confirmed by the accumulation of fructose in the media when the cells are grown on sucrose.

Example 2

Example 2 describes the addition of glucose isomerase to a lysine fermentation media containing sucrose.

An L-lysine-producing strain of *Corynebacterium*, for example, the strain deposited as NRRL B-11474, is grown in 20 ml of seed medium at about 30° C. for about 18 hours. Then 2 ml of the system is transferred to fermentation medium containing sucrose as at least one component of the carbons source and grown for 24 hours at 30° C. Glucose isomerase is added to the fermentation medium as either a liquid enzyme or as an immobilized enzyme. Sufficient enzyme is initially added to maintain an equilibrium in which about half of the sugars is fructose and the other half glucose. As will be recognized by those skilled in the art, the exact amount of glucose isomerase depends on the fermentation conditions. Continuous addition of glucose isomerase may be necessary to keep the activity of the glucose isomerase high enough for the conversion of fructose to glucose.

Example 3

Example 3 describes the production of a fructose export mutant in a ptsF mutant background strain of *C. glutamicum*.

Using a *C. glutamicum* ptsF mutant one could make a mutant of a putative fructose exporter. A *C. glutamicum* ptsF mutant will be subjected to mutagenesis. The ptsF mutant will be grown to mid-log phase, pelleted by centrifugation and resuspended in 2 ml of sterile TM buffer (This-HCl 6 g/l, maleic acid 5.8 µl, (NH4)2SO4 1.0 g/l, Ca(NO3)2 5 mg/l, MgSO4.7H2O 0.1 g/l, FeSO4.7H2O 0.25 mg/l adjusted to pH 6.0 with KOH). To the 2 ml cell suspension will be added 50 ul of a 5.0 mg/l solution of N-nitro-N-nitrosoguanidine (NTG) and then incubated at 30 C for 30 minutes. Then 10 mls of TM buffer was added and the cells pelleted by centrifugation, washed twice in TM buffer and resuspended in 4.0 ml of 0.1 M NaH2PO4 (phosphate buffer) adjusted to pH 7.2 using KOH. The cell suspensions were further diluted to achieve approximately 200-300 colonies per plate and plated out on the following minimal media.

| | |
|---|---|
| (NH4)SO4 | 10 g/l |
| KH2PO4 | 1 g/l |
| MgSO4*7H2O | 0.4 g/l |
| NaCl | 1 g/l |
| Urea | 2.5 g/l |
| MnSO4*H2O | 0.01 g/l |
| FeSO4*7H2O | 0.01 g/l |
| L-Alanine | 0.5 g/l |
| L-Methionine | 0.5 g/l |

-continued

| | |
|---|---|
| L-Threonine | 0.25 g/l |
| Biotin | 0.05 mg/l |
| Thiamine | 0.2 mg/l |
| Niacinamide | 0.05 gl/ |
| Sucrose | 1 g/l |
| Agar | 15 g/l |

After the colonies have grown up (2-5 days) the plates were overlaid with soft agar (0.7% w/v)) at 40 C containing Methylthiazolyldiphenyl-tetrazolium bromide (MTT) (0.2 mg/ml), phenazine methosulfate (2.5 mg/l), fructose dehydrogenase 2 U/ml and citric phosphate buffer pH 5.0. Colonies that excrete fructose will have blue halos and colonies that do not will not have halos. Colonies without blue halos will be picked and purified and tested to make sure they do not excrete fructose by growing on sucrose minimal media (same as above but without agar) and measuring if fructose is in the media. The ones that do not excrete fructose but grow on sucrose are deficient in the fructose exporter.

Example 4

Example 4 describes intracellular expression of glucokianse and glucose isomerase in a ptsF mutant strain of *C. glutamicum*.

Construction of a replicating plasmid containing glucokinase (SEQ ID NO: 6) and glucose isomerase (SEQ ID NO: 3). The following primers will be used to amplify by PCR the gene for glucose isomerase from *Streptomyces rubiginosus* DNA. The forward primer, ATTGACAATTAATCATCGGCTCGTATAATGTGTGGAATTGTGAGCGGATAACAATTT CACACAGGAAACAGCTATGAACTACCAGCCCACCCCCG (SEQ ID NO: 9), contains the tac promoter and ribosome binding site necessary for the expression of the gene. The reverse primer is, TCAGCCCCGGGCGCCCAGC (SEQ ID NO: 10). These two primers will amplify the glucose isomerase gene operationally linked to the tac promoter. This fragment will be cloned directly into the SmaI site of pD10 (U.S. Pat. No. 7,141,388). The clones will be screened for one in the correct orientation. This plasmid will be called pD10xylA.

The following primers will be used to clone the glucokinase gene from *C. glutamicum*.

```
The forward primer is,
                                    (SEQ ID NO: 11)
GAACGCGAGGGGGCACTCTTATGCCACAAAAACCGGCC
and the reverse primer is,
                                    (SEQ ID NO: 12)
CTAGTTGGCTTCCACTACAGAGCG.
```

These two primers will amplify the glucokinase gene which will be directly cloned into the EcoRV site in pD10xylA. Again the clones with the glucokinase gene will be screened for the proper orientation.

The correct clone called pD10xylAglk will contain the genes for glucose isomerase and glucokinase in a synthetic operon with the expression controlled by the tac promoter. The plasmid pD10xylAglk will be introduced into the fructose exporter mutant described in example 3 by electorporation as described in U.S. Pat. No. 7,141,388. Colonies will be selected for resistance to cloramphenicol. These colonies will containe the plasmid pD10xylAglk.

Having now fully described the present invention in some detail by way of illustration and example for purposes of clarity of understanding, it will be apparent to one of ordinary skill in the art, with the benefit of this disclosure, that the invention can be performed by modifying or changing the invention with a wide and equivalent range of conditions, formulations and other parameters thereof. Furthermore, it will be apparent to the skilled practitioner with the benefit of this disclosure that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference. None of the publications, patents and patent applications mentioned herein are admitted to be prior art.

We claim:

1. A method of producing lysine by fermentation, comprising:
   (a) growing a *Corynebacterium glutamicum* (*C. glutamicum*) strain in which the transferase activity of a fructose-phosphotransferase system II enzyme (fructose-PTS enzyme II) has been attenuated or blocked in a fermentation medium that contains cane sugar or beet sugar as the carbon source and that contains an amount of glucose isomerase effective to convert fructose to glucose in said fermentation medium; and
   (b) fermenting said microorganism to produce lysine, wherein the *C. glutamicum* strain having the fructose PTS enzyme II activity attenuated or blocked produces more lysine when grown in said fermentation medium than a comparative strain that is identical except for not having the PTS enzyme II activity attenuated or blocked.

2. The method of claim 1 wherein attenuation or blocking of the fructose-PTS is effected by disrupting or deleting the ptsF gene of said strain.

3. The method of claim 1, wherein said glucose isomerase is exogenously added to the fermentation medium.

4. The method of claim 1 wherein the fermentation medium further includes invertase in an amount effective to convert a portion of the sucrose to fructose and glucose in the fermentation medium.

5. The method of claim 1, wherein the *C. glutamicum* strain in which the transferase activity of the fructose PTS enzyme II has been attenuated or blocked further comprises a mutation that attenuates or blocks export of fructose from the strain.

6. The method of claim 5, wherein the *C. glutamicum* strain further comprises a glucose kinase gene that is overexpressed.

7. The method of claim 5, wherein the *C. glutamicum* strain further comprises a glucose isomerase gene that is overexpressed.

8. The method of claim 5, wherein the *C. glutamicum* strain further comprises a glucose kinase gene and a glucose isomerase gene that are overexpressed.

* * * * *